United States Patent
Kühlmeier

(10) Patent No.: US 8,316,716 B2
(45) Date of Patent: Nov. 27, 2012

(54) METHOD FOR INSPECTING AT LEAST ONE ROTOR BLADE OF A WIND TURBINE AND INSPECTION SYSTEM FOR AT LEAST ONE ROTOR BLADE OF A WIND TURBINE

(75) Inventor: Lennart Kühlmeier, Ringkobing (DK)

(73) Assignee: Vestas Wind Systems A/S, Aahrus N. (DK)

( * ) Notice: Subject to any disclaimer, the term of this patent is extended or adjusted under 35 U.S.C. 154(b) by 339 days.

(21) Appl. No.: 12/569,595

(22) Filed: Sep. 29, 2009

(65) Prior Publication Data

US 2010/0011862 A1 Jan. 21, 2010

Related U.S. Application Data

(63) Continuation of application No. PCT/DK2008/000120, filed on Mar. 28, 2008.

(30) Foreign Application Priority Data

Mar. 29, 2007 (DK) .................................. 2007 00487

(51) Int. Cl.
*G01N 29/14* (2006.01)
(52) U.S. Cl. ............................................. 73/660; 73/587
(58) Field of Classification Search .................... 73/660, 73/587; 416/1, 61; 702/42, 104
See application file for complete search history.

(56) References Cited

U.S. PATENT DOCUMENTS

| | | | |
|---|---|---|---|
| 5,421,204 A | 6/1995 | Svaty, Jr. | |
| 5,905,440 A * | 5/1999 | Julian et al. | 340/680 |
| 6,124,692 A | 9/2000 | Canada et al. | |
| 6,619,918 B1 * | 9/2003 | Rebsdorf | 416/1 |
| 6,785,637 B1 | 8/2004 | Wobben | |
| 6,940,186 B2 * | 9/2005 | Weitkamp | 290/44 |
| 7,322,794 B2 * | 1/2008 | LeMieux et al. | 416/40 |
| 7,334,989 B2 * | 2/2008 | Arelt | 416/2 |
| 7,400,054 B2 * | 7/2008 | Wesselink | 290/44 |
| 7,470,114 B2 * | 12/2008 | Bonnet | 416/226 |
| 8,021,110 B2 * | 9/2011 | Kerber | 416/1 |
| 8,021,112 B2 * | 9/2011 | Dinjus et al. | 416/1 |
| 8,043,048 B2 * | 10/2011 | Daniels et al. | 415/118 |

(Continued)

FOREIGN PATENT DOCUMENTS

| | | |
|---|---|---|
| DE | 10065314 A1 | 7/2002 |
| WO | 9957435 A1 | 11/1999 |
| WO | 0201172 A1 | 1/2002 |
| WO | 2006012827 A1 | 2/2006 |

OTHER PUBLICATIONS

Danish Search Report; PA 2007 00487; Oct. 24, 2007; 1 page.

(Continued)

*Primary Examiner* — J M Saint Surin

(74) *Attorney, Agent, or Firm* — Patterson & Sheridan, LLP

(57) ABSTRACT

A method for inspecting at least one rotor blade of a wind turbine for damage, such as subsurface blade cracks, includes the steps of: attaching at least one acoustic emission sensor to a surface of a rotor blade to be inspected, exciting oscillations in the rotor blade for a time period, measuring activity signals of the oscillations in the rotor blade with the at least one acoustic emission sensor, and detaching the at least one acoustic emission sensor from the surface of the rotor blade after the inspection. An inspection system for a rotor blade of a wind turbine is also contemplated.

18 Claims, 6 Drawing Sheets

U.S. PATENT DOCUMENTS

| | | | |
|---|---|---|---|
| 8,043,054 B2 * | 10/2011 | D et al. | 416/1 |
| 8,092,174 B2 * | 1/2012 | Egedal | 416/61 |
| 8,100,647 B2 * | 1/2012 | Godsk et al. | 416/1 |
| 8,120,522 B2 | 2/2012 | Tralshawala et al. | 342/25 F |
| 8,123,478 B2 * | 2/2012 | Ahmann | 416/1 |
| 8,123,480 B2 * | 2/2012 | Enevoldsen et al. | 416/61 |
| 2009/0169378 A1 * | 7/2009 | Menke | 416/1 |
| 2009/0232635 A1 * | 9/2009 | Menke | 415/17 |

OTHER PUBLICATIONS

International Search Report; PCT/DK2008/000120; Dec. 1, 2008; 3 pages.

* cited by examiner

METHOD FOR INSPECTING AT LEAST ONE ROTOR BLADE OF A WIND TURBINE AND INSPECTION SYSTEM FOR AT LEAST ONE ROTOR BLADE OF A WIND TURBINE

CROSS-REFERENCE TO RELATED APPLICATIONS

The present application is a continuation of pending International patent application PCT/DK2008/000120 filed on Mar. 28, 2008 which designates the United States and claims priority from Danish patent application PA 2007 00487 filed on Mar. 29, 2007, the content of which is incorporated herein by reference.

FIELD OF THE INVENTION

The invention relates to a method for inspecting a rotor blade of a wind turbine and an inspection system for a rotor blade of a wind turbine.

BACKGROUND OF THE INVENTION

The use of inspection for wind turbines has increased significantly in the recent years as the main wind turbine components and especially the rotor blades have increased in size and are designed closer to the material limits.

One known solution includes inspecting the rotor blade surface by eye for cracks and similar damage which is very time consuming and also ineffective in relation to subsurface damage.

Another known solution includes dismantling of the rotor blades from the wind turbine and performing more advanced inspections at an inspection center.

It is an object of the present invention to provide local inspection solutions for wind turbines without the abovementioned disadvantages in the prior art.

SUMMARY OF THE INVENTION

The invention provides a method for inspecting at least one rotor blade of a wind turbine for damage such as subsurface blade cracks, said method comprising the steps of:
 attaching at least one acoustic emission sensor to a surface of a rotor blade to be inspected,
 exciting oscillations in the rotor blade for a time period,
 measuring activity signals of the oscillations in the rotor blade with said at least one acoustic emission sensor, and
 detaching said at least one acoustic emission sensor from said surface of said rotor blade after said inspection.

Hereby is achieved an advantageous method for locally inspection of a wind turbine rotor blade by measuring the activity signal after having excited oscillations in the rotor blade.

It shall be emphasized that rotor blade inspection is considered to be a process of obtaining rotor blade data in a limited time period in order to establish the rotor blade status in relation to damage at the inspection time. The rotor blade data are obtained by temporary attaching an inspection system comprising said at least one acoustic emission sensors.

The measured activity signal is a measure of the health of the rotor blade which may be assessed locally on the site by the service people or brought back to an inspection center for further assessments.

In an aspect of the present invention said exciting of the rotor blade is established by introducing flap wise and/or edge wise oscillations manually e.g. at the rotor blade tip. Hereby is achieved an easy and advantageous method for creating oscillations in rotor blade resulting in activity signals revealing the health status of the rotor blade. A service worker may simply move the flexible rotor blade tip section back and forth in a uniformly manner for a time period. Hereby is created an oscillation in the rotor blade resulting in one type of activity signals if the rotor blade is healthy and others if the rotor blade has damage e.g. subsurface cracks.

In another aspect of the present invention said activity signals are measured with said at least one acoustic emission sensor in surface contact with the structural means of the rotor blade e.g. positioned on the outer surface just above the blade spar beam of the rotor blade or on the blade spar beam. It is especially important to inspect the structural means of the rotor blade as undetected damage in the structural means may result in rotor blade failure and significant downtime for the wind turbine.

In a further aspect of the present invention an acoustic coupling agent is applied to the relevant rotor blade surface before the positioning of said at least one acoustic emission sensor e.g. with a mounting bracket holding each sensor in place on the surface. Hereby it is possible to establish a defined and firm connection between the outer surface of the rotor blade and the sensor. Further, the system may easily and quickly be removed from the rotor blade without leaving marks if the bracket is only adhered to the surface.

In an even further aspect of the present invention at least two acoustic sensors are positioned opposite each other on the leeward and windward side of the rotor blade. Hereby is the rotor blade evenly divided between one or more sets of two sensors with a similar measuring result in the set if the rotor blade is healthy.

In an aspect of the present invention said at least one acoustic sensor is attached to the outer rotor blade surface in a centre position in relation to leading and trailing edges and/or the blade spar beam of the blade. Hereby is achieved an advantageous method for detecting damage centrally in the rotor blade and strengthening structure such as just above the longitudinal centre line of the rotor spar beam.

In an aspect of the present invention said at least one acoustic sensor is attached to the outer rotor blade surface or to an internal rotor blade surface or to the outer and an internal rotor blade surface in combination. Hereby it is advantageously possible to detect structural damage of the rotor blade such as subsurface cracks by using acoustic emission sensors.

In another aspect of the present invention said at least one acoustic sensor is attached to the outer rotor blade surface within a third of the rotor blade length from the rotor blade tip. Hereby is achieved an advantageous method for detecting propagated damage at the tip-spar transfer region of a rotor blade e.g. internal damage in the transfer region where the rotor blade spar ends in direction toward the tip.

In an aspect of the present invention said at least one acoustic sensor is attached to the internal rotor blade surface within half of the rotor blade length from the rotor blade hub. Hereby is achieved an advantageous method for closely detecting propagated damage at the root-spar region of a rotor blade e.g. internal damage in the inner region of the rotor blade spar.

In an aspect of the present invention said exciting of the rotor blade and measurement of activity signals are performed for a time period of at least 5 seconds and preferably for a time period of at least 10 seconds. Hereby it is possible to achieve reliable and conclusive measurements of activity signals in the rotor blades.

In further aspect of the present invention the measured data are transferred from said at least one acoustic emission sensor to a portable acoustic emission unit for storage and/or investigation and/or displaying. Hereby it is possible to store the measured data for later assessment or for an on site inspection e.g. by displaying the measured acoustic spectrum in a display of the unit. The unit may preferably be strapped to the rotor blade in proximity of the at least one sensor in order to create an acoustic emission system which is easy to handle and compact.

In other aspects of the present invention the data transfer from said at least one acoustic emission sensor is performed by cables or by wireless communication. Hereby it is advantageously possible to perform inspection when the rotor blades are at standstill or rotating.

In another aspect of the present invention said rotor blade initially is brought to a standstill and locked preferably in a position facing downwards. Hereby is established a defined and stable position for performing the inspection of the rotor blade and especially creating the oscillation in the rotor blade.

The rotor is performing rotational movement during inspection of said at least one blade in a further aspect of the present invention. The rotating of the wind turbine rotor ensures that significant flap and/or edge wise oscillations may be introduced to the rotor blades and especially larger oscillations than by a manual exciting at the blade tip.

The rotor is performing an emergency stop sequence during inspection of said at least one blade in an even further aspect of the present invention. Hereby are very large flap wise oscillations in the rotational sequence achieved as the rotor blades are abruptly forced forward until the rotor is at a standstill.

In an aspect of the present invention the signals of said at least one acoustic emission sensor is compared with pre-established reference level values. Hereby it is possible in a simple manner to detect whether a rotor blade is healthy by being below a pre-established reference level value or damaged by being above a pre-established reference level value.

In an aspect of the present invention the signals from acoustic emission sensors in proximity of each other is used for directional damage detection. With the use of sets of sensors in proximity of each other it is possible not only to detect damage but also to establish the direction of the damage by directional intersecting the acoustic emission signals.

Damage of the rotor blade may for example arise from different circumstances which have occurred during use such as lightning hits on the rotor blade. Consequently it may in some instances be sufficient and advantageously to only inspection predefined areas in a given type of rotor blades e.g. areas wherein the chance of damage occurrence is significantly higher than other rotor blade areas.

The invention also provides an inspecting system for measuring excited oscillations in a rotor blade of a wind turbine, said system comprising
  at least one acoustic emission sensor attached to the outer surface of the rotor blade with attachment means, and
  a portable acoustic emission unit for storage and/or investigation and/or displaying measured data transferred from said at least one acoustic emission sensor via connection means.

Hereby is created an advantageous system which may be used in performing an inspection method of a wind turbine rotor blade without dismantling the rotor blade.

In an aspect of the present invention said attachment means are one or more mounting brackets and an acoustic coupling agent applied to the relevant rotor blade surface. Hereby is achieved an advantageous embodiment of the invention.

In another aspect of the present invention the number of acoustic emission sensors is at least two and preferably between two and 16 sensors positioned attached to a surface of the rotor blade. Hereby it is advantageously possible to perform inspections on large parts of the rotor blade if not all of the rotor blade.

BRIEF DESCRIPTION OF THE DRAWINGS

The invention will be described in the following with reference to the figures in which.

DETAILED DESCRIPTION OF THE INVENTION

Figure 1:
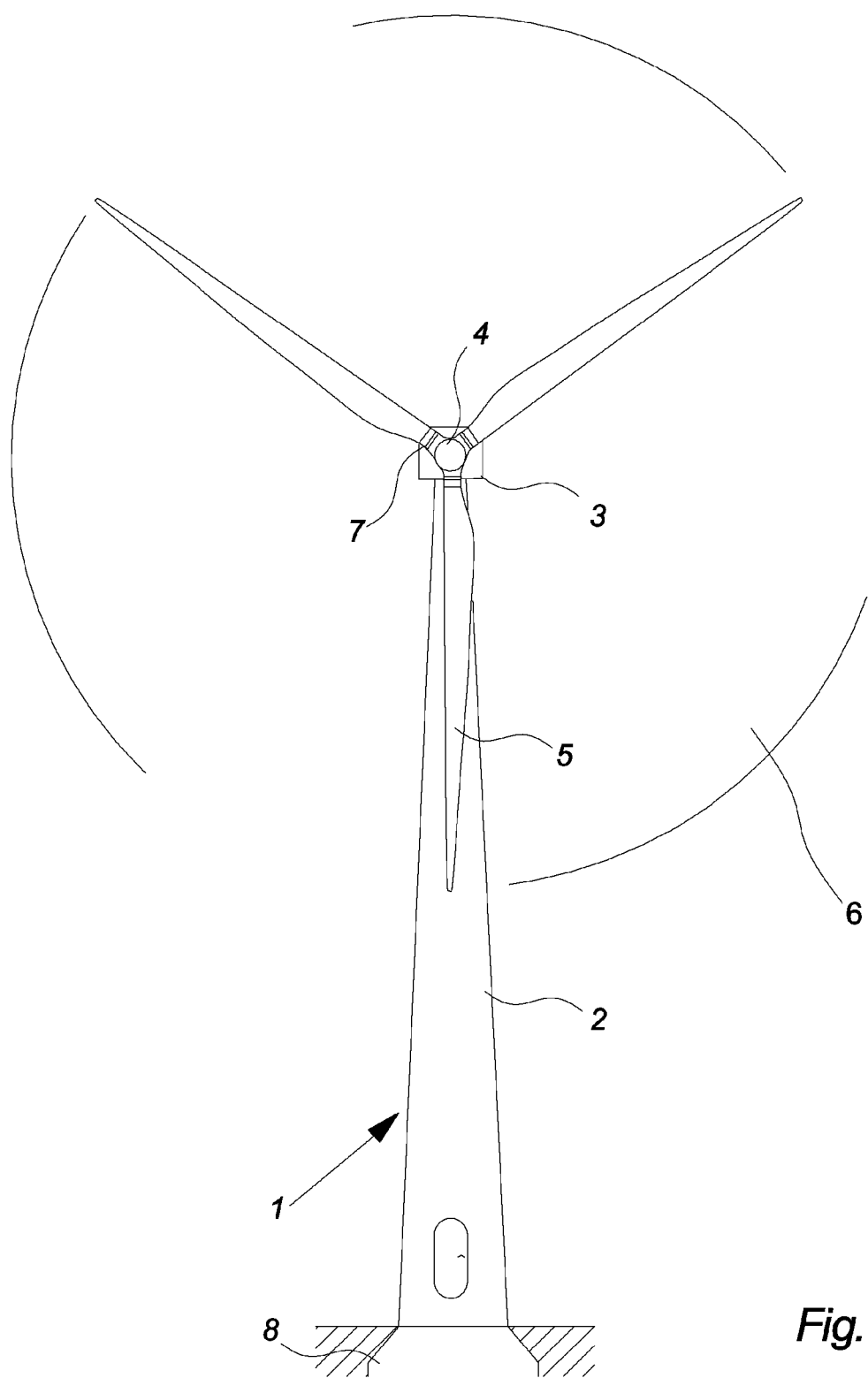
FIG. 1 illustrates a front view of a wind turbine.

FIG. 1 illustrates a front view of a modern wind turbine 1 with a tower 2 positioned on a foundation 8. A wind turbine nacelle 3 and hub 4 is positioned on top of the tower.

The wind turbine rotor 6, comprising at least one rotor blade such as two or three wind turbine rotor blades 5 as illustrated, is connected to the wind hub 4 through pitch mechanisms 7. Each pitch mechanism includes a blade bearing and pitch actuating means which allows the blade to pitch.

Figure 2:
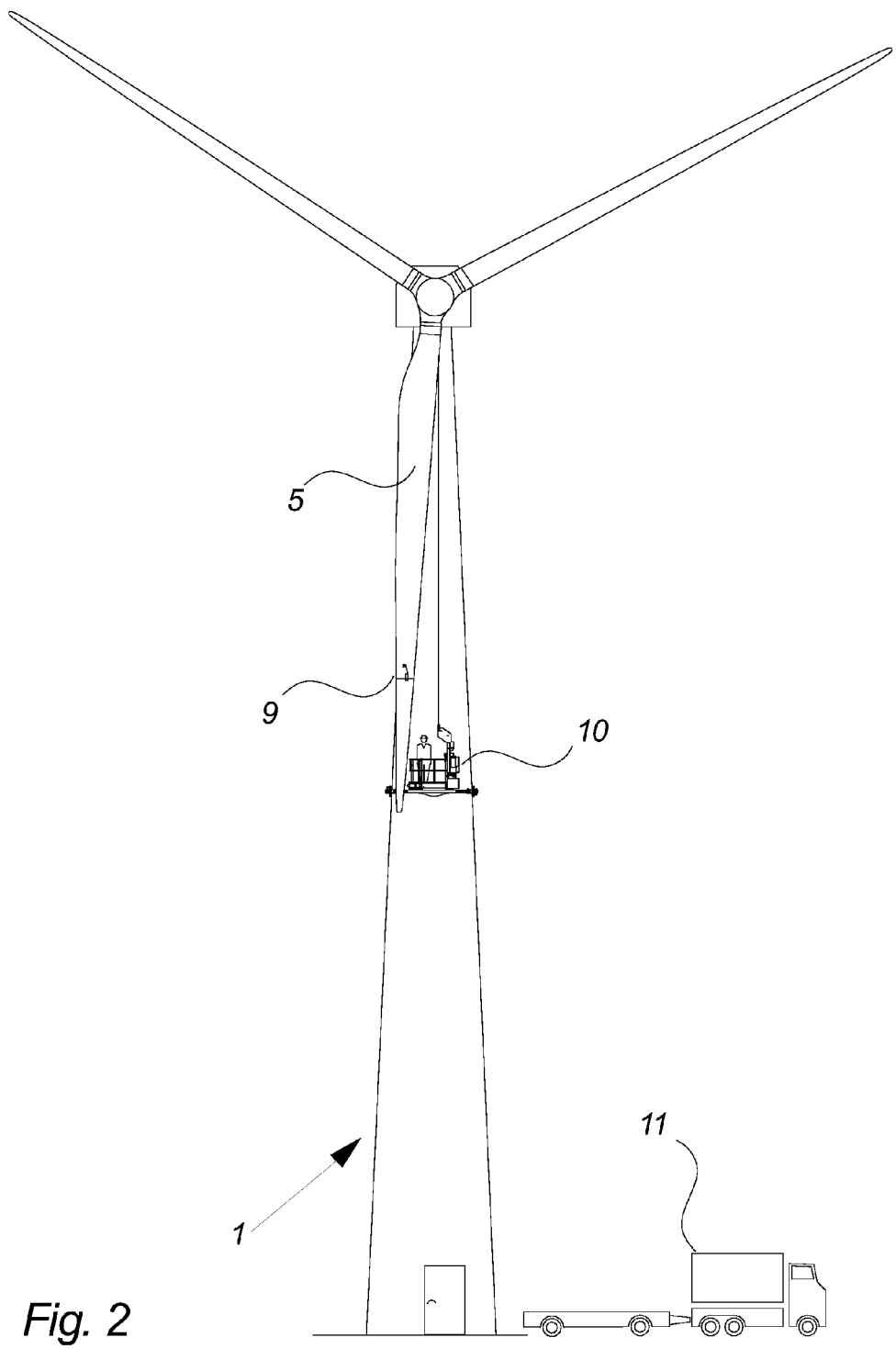
FIG. 2 illustrates a rotor blade of a wind turbine being inspected by workers on a service platform as one embodiment of the invention.

FIG. 2 illustrates a rotor blade 5 of a wind turbine 1 being inspected by workers on a service platform 10 in one embodiment of the invention.

Initially the rotor has been locked in a position, where the rotor blade subject to inspection is pointing downwards and the area under the tip of the lowest blade has been secured using warning tape (not shown on the figure).

Hereafter is a service platform 10 with workers lifted from an inspection vehicle 11 to a rotor blade position and an inspection system 9 is attached to the outer surface of the rotor blade.

The service platform 10 is lowered to the tip section of the blade and an inspection is performed by introducing flap and/or edge wise oscillations to the rotor blade e.g. by the worker moving the tip back and forth in a time period.

The inspection system 9 measures the acoustic activity in the rotor blade 5 excited by the introduced oscillations. The measured result may be compared with pre-established reference level values.

The workers remove the inspection system from the rotor blade when the inspection has been completed and the inspection is subsequently performed on the other rotor blades in the same manner.

A platform lifted by a crane, a hoist or similar solutions may also be used instead of the illustrated self-lifting service platform.

Figure 3:
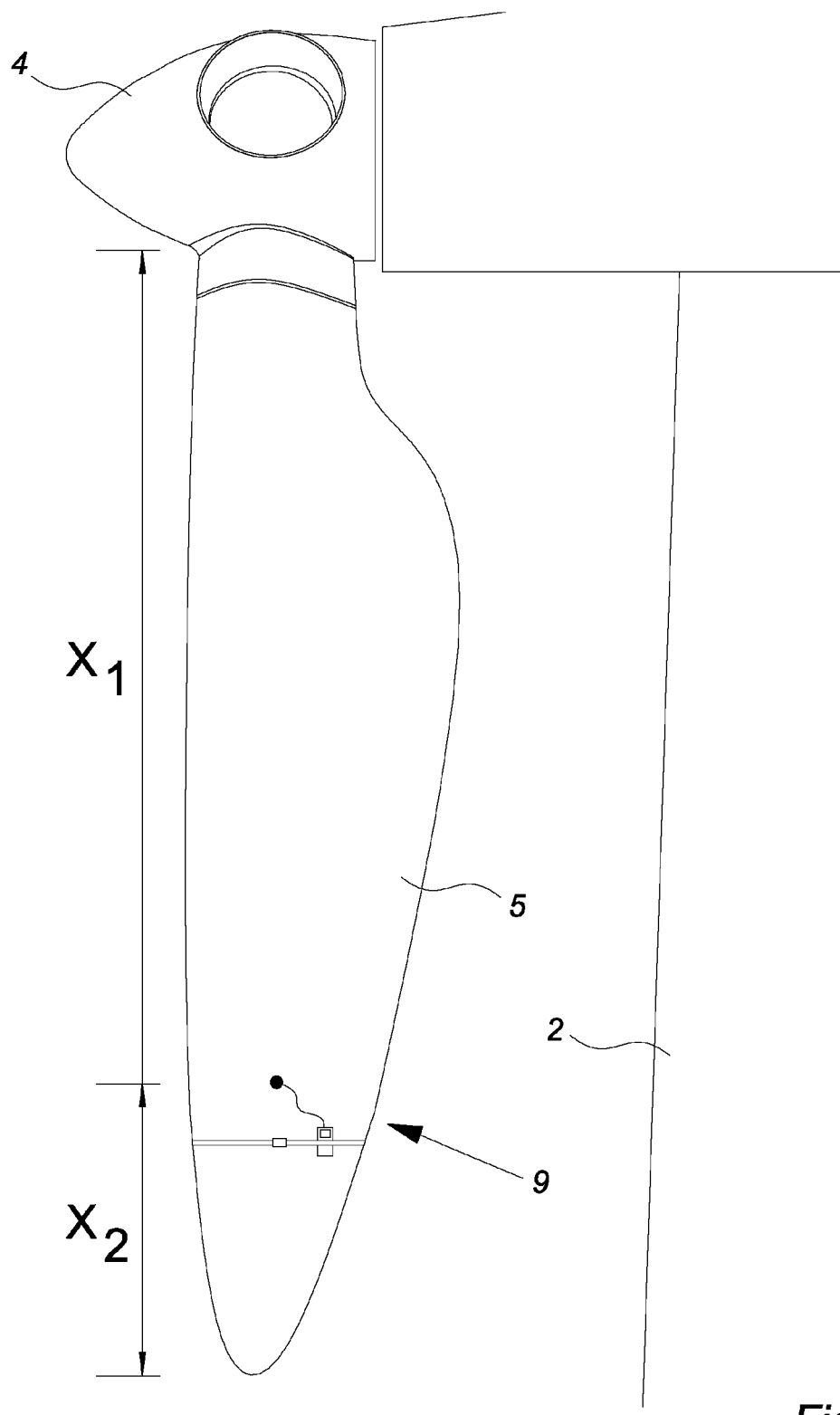
FIG. 3 illustrates a first embodiment of the invention wherein the rotor blade has an acoustic emission system attached to the outer surface in a distance $X_2$ from the rotor blade tip.

FIG. 3 illustrates a first embodiment of the invention wherein the rotor blade has an acoustic emission system 9 attached to the outer surface in a distance $X_2$ from the rotor blade tip.

The length of the rotor blade corresponds to $X_1+X_2$ wherein $X_1$ is the length from the hub 4 to the position of the acoustic emission sensor and $X_2$ is the length from the rotor blade tip to the acoustic emission sensor.

The ratio between X1 and X2 is in one embodiment of the invention at least 2 to 1 and preferably approx. 3 to 1.

Figure 4:
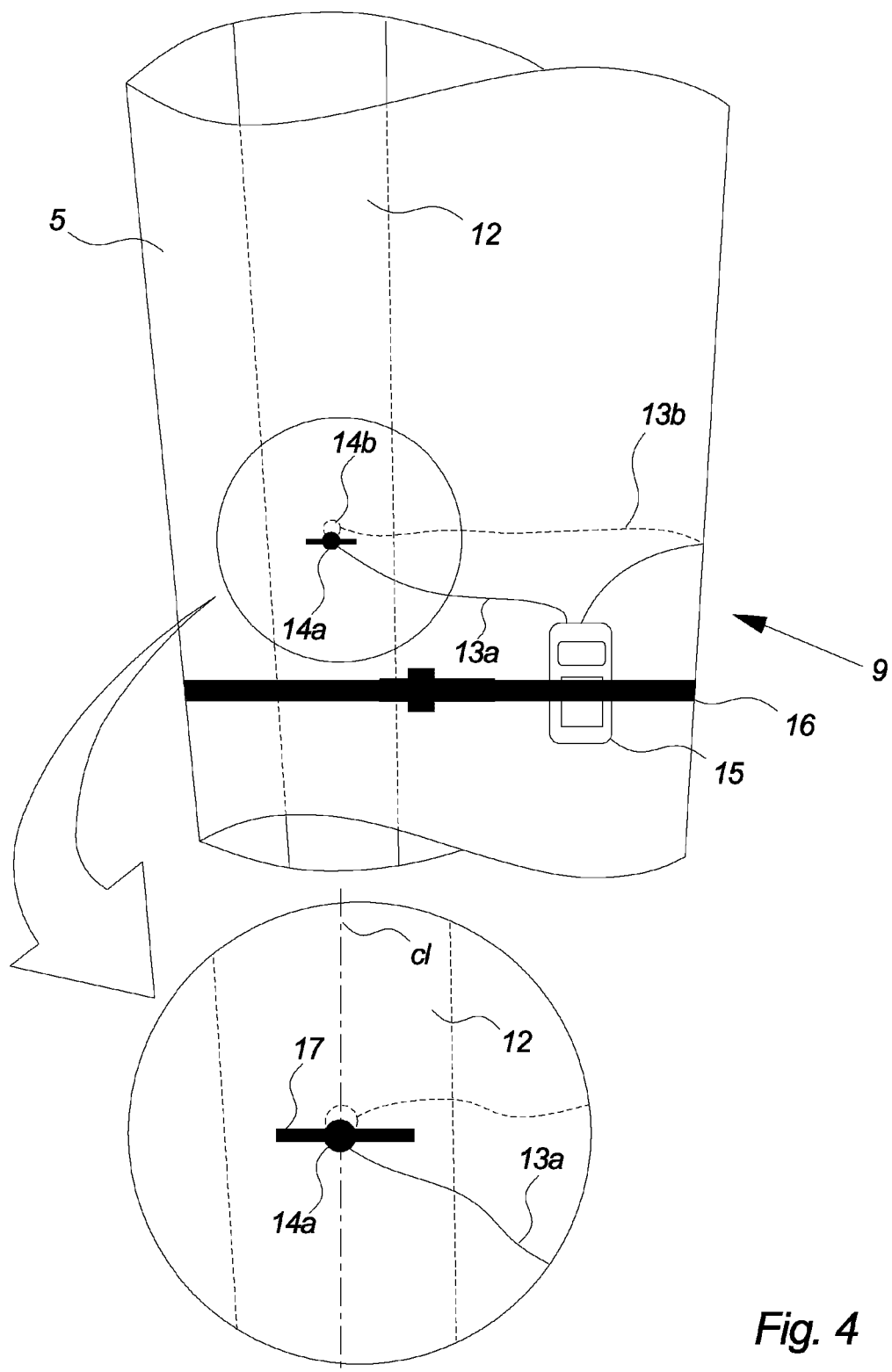
FIG. 4 illustrates a sectional view of a wind turbine rotor blade with the acoustic emission system attached.

FIG. 4 illustrates a sectional view of a wind turbine rotor blade 5 with the acoustic emission system 9 attached.

The system 9 includes two acoustic emission sensors 14*a*, 14*b* connected to an acoustic emission inspection unit 15 via cable connection means 13*a*, 13*b*. The unit is portable and battery powered and may comprise storage means, processor means for analyzing the measured data and a display.

The two sensors 14*a*, 14*b* are preferably attached to the leeward and windward side of the rotor blade 5, respectively. The sensors are positioned opposite each other and attached with mounting brackets 17 after having applied an acoustic coupling agent on the rotor blade surface.

The acoustic emission inspection unit 15 is preferably secured to the blade by using a ratchet strap before the sensor cables are connected to unit inputs.

The enlarged area of the figure illustrates the sensor position on the outer surface of the rotor blade in further details. The two sensors 14*a*, 14*b* are illustrated as attached above the longitudinal centre line (cl) of the spar beam 12 and on the leeward and windward side of the rotor blade 5.

Figures 5A, 5B, 5C:
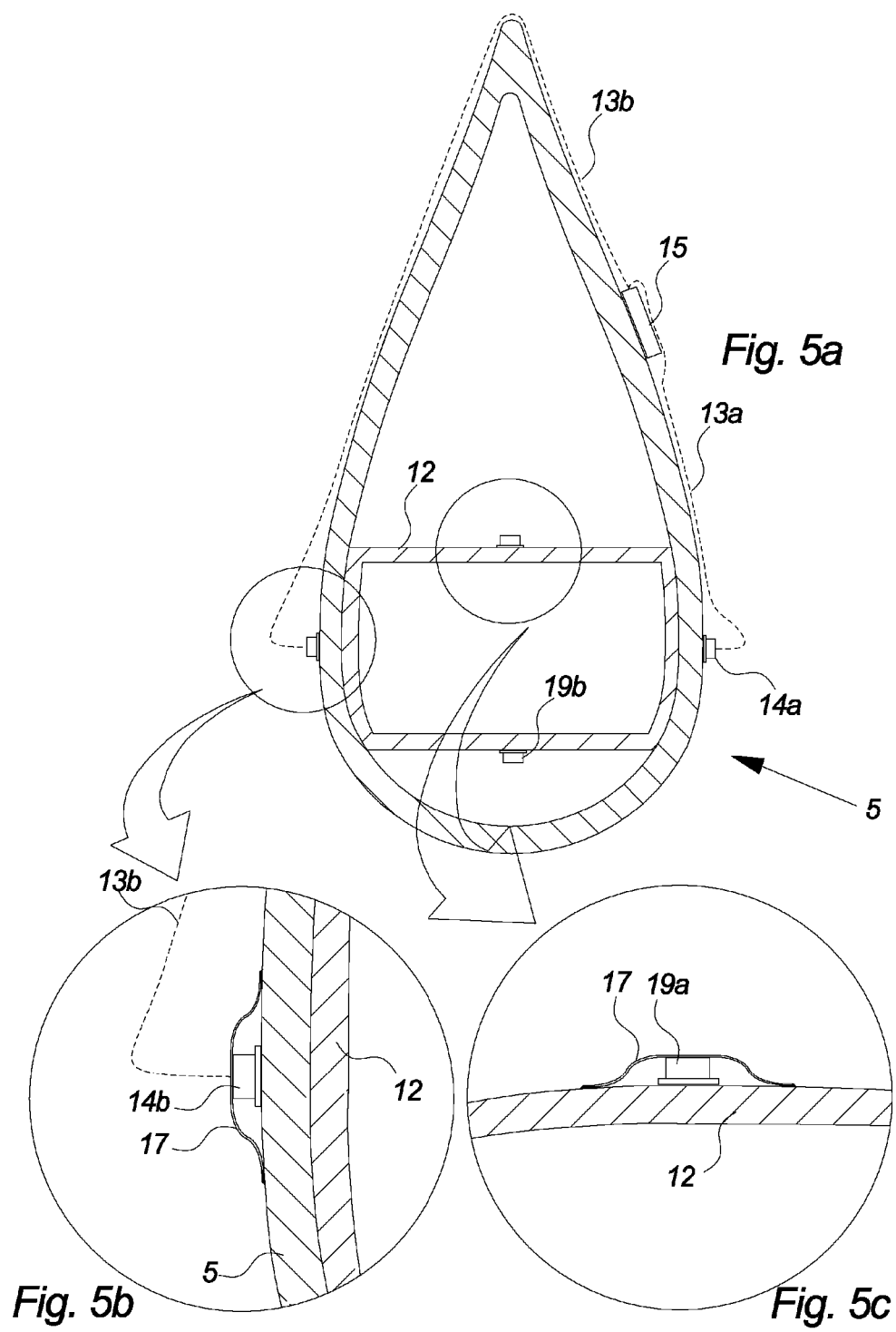
FIGS. 5a-5c illustrate a cross sectional view of the rotor blade with acoustic emission sensors mounted on different rotor blade surfaces.

FIGS. 5*a*-5*c* illustrate a cross sectional view of the rotor blade with acoustic emission sensors mounted on different rotor blade surfaces.

FIG. 5*a* illustrates a cross sectional view of the rotor blade 5 with two acoustic emission sensors 14*a*, 14*b* and an acoustic emission inspection unit 15 mounted on the outer rotor blade surface as well as two acoustic emission sensors 19*a*, 19*b* mounted on the surface of a strengthening structure shown as the spar beam 12 of the rotor blade.

The different sensor configurations on outer and inner surfaces of the rotor blade may be combined within the same configuration or be separate configurations i.e. either the use of outer or inner acoustic emission sensors.

The enlarged area of FIG. 5*b* illustrates the attachment of the sensor 14*b* with mounting bracket 17 on the outer surface of the rotor blade in further details. The bracket is adhered to the rotor blade surface in both ends and forces the sensor against the surface. The bracket may be adhered to surface by using bits of tape or by having an adhesive area at the ends. The sensor is connected to the acoustic emission unit with a cable 13*b* but may also data communicate wirelessly.

The enlarged area of FIG. 5*c* illustrates the attachment of a sensor 19*a* with mounting bracket 17 on the surface of the rotor spar beam 12 in further details. The bracket is adhered to the surface in both ends and forces the sensor against the surface. The bracket may be adhered to surface by using bits of tape or by having an adhesive area at the ends.

The sensor has wireless data transmission means which may establish a wireless data connection to the acoustic emission unit. The acoustic emission unit is preferably positioned in another place than the rotor blade e.g. in an inspection vehicle as illustrated in FIG. 2.

The cabled sensor and unit configuration of FIG. 5*b* may preferably be used in an inspection method where the rotor blade initially is brought to a standstill and locked e.g. in a position facing downwards.

A wireless sensor configuration with a remote acoustic emission unit in relation to the rotor blade may also be used in inspection methods where the wind turbine rotor is rotating e.g. during an emergency stop sequence.

Figure 6:
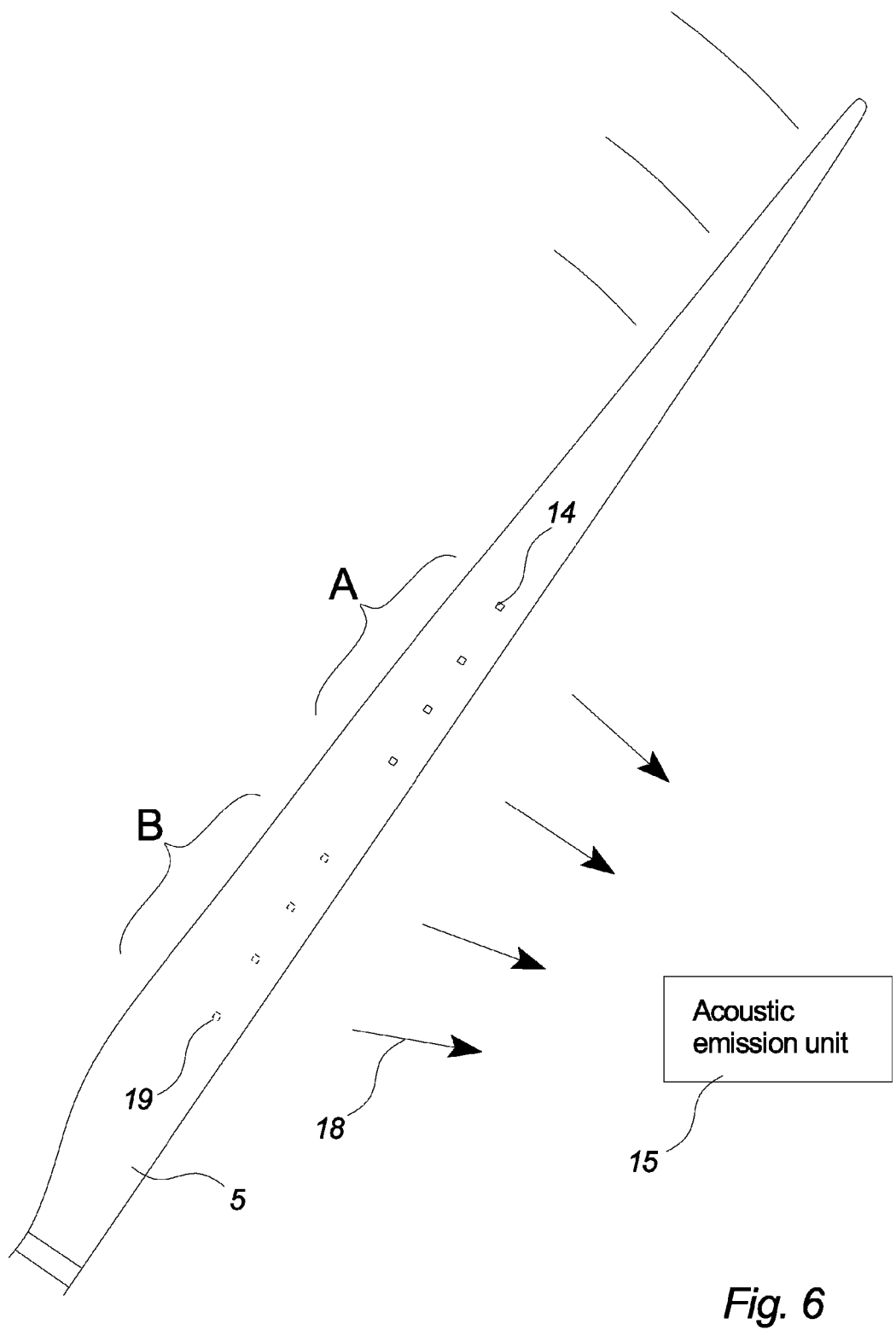
FIG. 6 illustrates a rotor blade with different acoustic emission sensor configurations mounted as further embodiments of the invention.

FIG. 6 illustrates schematically a rotor blade with different acoustic emission sensor configurations mounted as further embodiments of the invention.

The group of acoustic sensors marked "A" is illustrated as sensors attached on the outer surface of the rotor blade by the use of solid lines. The group of acoustic sensors marked "B" is illustrated as sensors attached on an inner surface of the rotor blade by the use of dotted lines. The groups of sensors are further illustrated as transferring data wirelessly to a remote positioned acoustic emission unit 15 while the rotor blade is rotating.

The different sensor configurations on the outer and inner surfaces of the rotor blade may be combined within the same configuration or be separate configurations i.e. either the use of outer or inner acoustic emission sensors.

The invention described has been exemplified above with reference to specific examples of strengthening structures in the rotor blades i.e. rotor blades with an internal blade spar. However, it should be understood that the invention is not limited to the particular examples but may be designed and altered in a multitude of varieties within the scope of the invention as specified in the claims e.g. with the strengthening structure integrated in the rotor blade surface such as a carbon-wood configuration.

What is claimed is:

1. A method for inspecting at least one rotor blade of a wind turbine, comprising:
   while the rotor blade is oscillating, measuring activity signals of the oscillations in the rotor blade with an acoustic emission sensor that is attached to at least one of (i) an outer rotor blade surface within a third of a rotor blade length of the rotor blade as measured from a rotor blade tip and (ii) an internal rotor blade surface within half of a rotor blade length of the rotor blade as measured from a rotor blade hub; and
   determining damage to the rotor blade based on the measured activity signals.

2. The method according to claim 1, wherein the oscillations are caused by manually introducing at least one of flap and edge wise oscillations.

3. The method according to claim 1, wherein the activity signals are measured with the acoustic emission sensor in surface contact with structural means of the rotor blade.

4. The method according to claim 1, further comprising:
   positioning the acoustic emission sensor such that a contact surface of the acoustic emission sensor faces the surface of the rotor blade or a surface of an element within the rotor blade; and
   before positioning the acoustic emission sensor, applying an acoustic coupling agent between the contact surface and the surface of the rotor blade or the surface of the element.

5. The method according to claim 1, where at least two acoustic sensors are positioned opposite each other on leeward and windward sides of the rotor blade.

6. The method according to claim 1, wherein the acoustic sensor is attached to at least one of an outer rotor blade surface in a centre position in relation to leading and trailing edges of the rotor blade and a spar beam of the rotor blade.

7. The method according to claim 1, wherein the acoustic sensor is attached to the outer rotor blade surface or to the internal rotor blade surface or to the outer and the internal rotor blade surfaces in combination.

8. The method according to claim 1, wherein the measured activity signals are transferred from the acoustic emission sensor to a portable acoustic emission unit to be at least one of stored, investigated and displayed.

9. The method according to claim 8, wherein the transfer of the activity signals from the acoustic emission sensor to the portable acoustic emission unit is performed by cables or by wireless communication.

10. The method according to claim 1, wherein measuring the activity signals is performed while the rotor blade is at a standstill and locked.

11. The method according to claim 1, wherein the activity signals detected by the acoustic emission sensor are compared with pre-established reference level values.

12. The method according to claim 1, wherein activity signals detected by at least two acoustic emission sensors in proximity of each other are used for directional damage detection.

13. An inspection system for measuring oscillations in at least one rotor blade of a wind turbine, said system comprising
an acoustic emission sensor attached to at least one of (i) an outer rotor blade surface within a third of a rotor blade length of the rotor blade as measured from a rotor blade tip and (ii) an internal rotor blade surface within half of a rotor blade length of the rotor blade as measured from a rotor blade hub, the acoustic emission sensor configured to produce a signal based on the oscillations of the rotor blade; and
a portable acoustic emission unit configured to at least one of store, investigate and display the signal, wherein the signal is transferred from the one acoustic emission sensor via at least one of cable and wireless connection means.

14. The inspection system according to claim 13, further comprising attachment means for attaching the acoustic emission sensor, wherein the attachment means comprise one or more mounting brackets and an acoustic coupling agent.

15. The inspection system according to claim 13, wherein at least two acoustic emission sensors are attached to the rotor blade.

16. A method for inspecting at least one rotor blade of a wind turbine, comprising:
while the rotor blade is oscillating, measuring activity signals of the oscillations in the rotor blade with an acoustic emission sensor that is located on a surface of the rotor blade or within the rotor blade; and
determining damage to the rotor blade based on the measured activity signals, wherein the activity signals are measured for a time period of at least 5 seconds.

17. A method for inspecting at least one rotor blade of a wind turbine, comprising:
while the rotor blade is oscillating, measuring activity signals of the oscillations in the rotor blade with an acoustic emission sensor that is located on a surface of the rotor blade or within the rotor blade, wherein the activity signals are measured while a rotor comprising the rotor blade is rotating using a rotor hub, and wherein the activity signals are measured while the rotor is performing an emergency stop sequence; and
determining damage to the rotor blade based on the measured activity signals.

18. The method of claim 17, wherein the acoustic emission sensor is associated with a different acoustic emission sensor, wherein the two acoustic emission sensors are located on the surface of the rotor blade and are positioned substantially opposite each other on a leeward side and a windward side of the rotor blade.

* * * * *